US011422121B2

(12) United States Patent
Pessi et al.

(10) Patent No.: US 11,422,121 B2
(45) Date of Patent: Aug. 23, 2022

(54) DEVICE, METHOD AND KIT FOR DISSOLUTION TESTING

(71) Applicant: NANOFORM FINLAND OY, Helsinki (FI)

(72) Inventors: Jenni Pessi, Helsinki (FI); Sami Svanbäck, Helsinki (FI); Ilkka Lassila, Helsinki (FI); Jouko Yliruusi, Vantaa (FI)

(73) Assignee: NANOFORM FINLAND OYJ, Helsinki (FI)

( * ) Notice: Subject to any disclaimer, the term of this patent is extended or adjusted under 35 U.S.C. 154(b) by 297 days.

(21) Appl. No.: 16/330,004

(22) PCT Filed: Sep. 5, 2017

(86) PCT No.: PCT/FI2017/050624
§ 371 (c)(1),
(2) Date: Mar. 1, 2019

(87) PCT Pub. No.: WO2018/060547
PCT Pub. Date: Apr. 5, 2018

(65) Prior Publication Data
US 2019/0204286 A1    Jul. 4, 2019

(30) Foreign Application Priority Data
Sep. 29, 2016  (FI) ................................. 20165728

(51) Int. Cl.
*G01N 33/15*  (2006.01)
*G01N 13/00*  (2006.01)
(Continued)

(52) U.S. Cl.
CPC ............... *G01N 33/15* (2013.01); *G01N 1/36* (2013.01); *G01N 13/00* (2013.01);
(Continued)

(58) Field of Classification Search
CPC .. G01N 2013/006; G01N 33/15; G01N 13/00; G01N 2001/2866; G01N 1/36; G01N 2035/00198
See application file for complete search history.

(56) References Cited

U.S. PATENT DOCUMENTS 6,929,782 B1 *  8/2005  Ciliberto ................. B01L 3/508
                                                422/561
8,796,028 B2 *  8/2014  Hollander ............... B01L 3/508
                                                436/17
(Continued)

FOREIGN PATENT DOCUMENTS

EP    2 182 342 A1    5/2010
JP    2008-175603 A    7/2008
(Continued)

OTHER PUBLICATIONS

Gerard Bredael et al: "A Strategy for Quality Conlrol Dissolution Method Development for Immediate-Release Solid Oral Dosage Forms", Dissolution Technologies, vol. 22, No. 3, Jan. 1, 2015 (Jan. 1, 2015), US, pp. 10-16, XP055425420, ISSN: 1521-298X, DOI: 10.14227/DT220315P10.

(Continued)

*Primary Examiner* — Rebecca M Fritchman
(74) *Attorney, Agent, or Firm* — Nixon & Vanderhye

(57) ABSTRACT

Disclosed are devices and methods for dissolving sample substances such as drug molecules. Also disclosed is use of the method for device for testing dissolution rates of the sample substances. It utilizes lyophilic matrices that create conditions for discriminating the dissolved sample substance from undissolved sample substances. This is aimed at preventing dispersion of the undissolved sample substance to avoid any substantial membrane effects.

7 Claims, 9 Drawing Sheets

(51) Int. Cl.
*G01N 1/36* (2006.01)
*G01N 35/00* (2006.01)
*G01N 1/28* (2006.01)

(52) U.S. Cl.
CPC ........... *G01N 2001/2866* (2013.01); *G01N 2013/006* (2013.01); *G01N 2035/00198* (2013.01)

(56) References Cited

U.S. PATENT DOCUMENTS

| | | | | |
|---|---|---|---|---|
| 2007/0141147 | A1* | 6/2007 | Heil | A61K 9/5084 424/468 |
| 2011/0229380 | A1 | 9/2011 | Sheu | |
| 2015/0247864 | A1* | 9/2015 | Mrsny | G01N 13/00 436/86 |

FOREIGN PATENT DOCUMENTS

| | | |
|---|---|---|
| JP | 2015-535937 A | 12/2015 |
| WO | 0206518 A1 | 1/2002 |
| WO | 2014/053840 A1 | 4/2014 |
| WO | 2016/055696 A1 | 4/2016 |

OTHER PUBLICATIONS

International Search Report, dated Jan. 12, 2017, from corresponding PCT/FI2017/050624 application.
FI Search Report, dated Apr. 26, 2017, from corresponding FI 20165728 application.
Son et al., "Development of a standardized dissolution test method for inhaled pharmaceutical formulation," International Journal of Pharmaceutics, vol. 382, 2009, pp. 15-22.

* cited by examiner

DEVICE, METHOD AND KIT FOR DISSOLUTION TESTING

FIELD

The invention relates generally to devices and methods for dissolving sample substances such as drug molecules, in particular nanoparticles of drug molecules. The invention also relates to the use of the method and device for testing dissolution rates of the sample substance, and a kit to operationalize the method.

BACKGROUND

The dissolution rate of a drug is one of the primary physicochemical properties determined and modified during the drug discovery and development process. A way to increase the dissolution rate is to decrease the particle size. However, the study of dissolution rates of small particles, in particular nanoparticles, may be challenging. For example, it might be difficult to separate the dissolved fraction from non-dissolved particles for analysis.

The United States Pharmacopoeia (USP) I (basket) and II (paddle) methods have been modified for nanoparticle dissolution studies. Problems with the modified methods include migration of nanoparticles to interfaces e.g. by floating or adhesion, and by diffusional barriers (e.g. gelatin or dialysis membranes). The methods also require large amounts of solute and solvent with tedious sample preparation and separation steps before analysis. Separation steps such as filtration and centrifugation are often ineffective with nanoparticles and may significantly affect the dissolution processes. Additionally, adsorption to equipment and containers might become an issue. Therefore, these methods may be impractical when studying nanoparticle dissolution.

The USP IV flow-through apparatus has been found to be applicable for nanoparticle dissolution studies. However, the use of this apparatus has challenges related to filtering. Too large filter pore size leads to particles escaping and consequently to overestimating the dissolution rate, while too narrow pore size leads to clogging and even breaking of the filter.

Drug nanoparticles can be analyzed as tablets and as admixed with gel matrices. However, the tableting process may alter the physical form of the drug. It has also been found that particles may detach from the tablet surface during dissolution, thus invalidating the dissolution tests. Analysis of dissolution tests of nanoparticles admixed with gel matrices, in turn, may be complicated by the diffusion of the drug in the matrix.

Accordingly, there is a need for new methods and devices for determining dissolution rates of sample substances that are suitable also for nanoparticles.

SUMMARY

The following presents a simplified summary in order to provide a basic understanding of some aspects of various embodiments of the invention. The summary is not an extensive overview of the invention. It is neither intended to identify key nor critical elements of the invention, nor to delineate the scope of the invention. The following summary merely presents some concepts of the invention in a simplified form as a prelude to a more detailed description of exemplifying embodiments of the invention.

In accordance with the invention, there is provided a new device for dissolving a sample substance, the device comprising
a shell matrix comprising a first lyophilic material, and
a cage comprising at least one hole.

According to the invention, the shell matrix is adapted to cover the sample substance to form a shell matrix-sample substance system. The shell matrix-sample system is adapted to be inserted into the cage.

In accordance with the invention, there is provided also a new method for dissolving a sample substance, the method comprising
providing a sample substance,
covering the sample substance with a shell matrix comprising a first lyophilic material to form a shell matrix-sample substance system,
inserting the shell matrix-sample substance system into a cage comprising at least one hole, and
exposing the cage comprising shell matrix-sample substance system to a medium capable of dissolving the sample substance.

In accordance with the invention, there is provided also a new method for determining one of more dissolution properties of a sample substance, the method comprising
dissolving the sample substance into a dissolution medium by a method according to any of claims 6-12, and
determining at least one dissolution property of the sample substance in the dissolution medium.

In accordance with the invention there is also provided a method for controlling a process for producing a substance, the method comprising,
(i) producing a substance,
(ii) providing a sample substance by collecting a sample of the substance,
(iii) determining one or more dissolution properties of the sample substance according to claim 13,
(iv) comparing the one of more dissolution properties of the sample substance to one or more predetermined dissolution properties, and
(v) optionally modifying the producing based on the comparing.

In accordance with the invention, there is also provided a kit for use in a method according to any of claims 6-14, comprising a device according any of claims 1-5, and a lyophilic material for a sample substance.

A number of exemplifying and non-limiting embodiments of the invention are described in accompanied dependent claims.

Various exemplifying and non-limiting embodiments of the invention both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of also unrecited features. The features recited in depending claims are mutually freely combinable unless otherwise explicitly stated. Furthermore, it is to be understood that the use of "a" or "an", i.e. a singular form, throughout this document does not exclude a plurality.

BRIEF DESCRIPTION OF DRAWINGS

The exemplifying and non-limiting embodiments of the invention and their advantages are explained in greater detail below with reference to the accompanying drawings, in which.

DESCRIPTION

According to one embodiment the present invention concerns a device and a method for dissolving a sample substance. Exemplary sample substances are organic substances in the form of granules, films, suspension, lipids, emulsions, more preferably of powder-like substances, most preferably nanoparticles. As defined herein an "organic substance" is a molecule containing carbon, excluding carbon containing alloys, and relatively small number of carbon-containing compounds such as metal carbonates and carbonyls, simple oxides of carbon and cyanides, as well as allotropes of carbon and simple carbon halides and sulfides which are considered inorganic. Exemplary organic substrates used in the present technology are biologically active materials including medicaments and their pharmaceutically acceptable organic and inorganic salts.

A non-limiting list of exemplary classes of biologically active materials that may be of interest to the technology include analgesics, antagonists, anti-inflammatory agents, anthelmintics, antianginal agents, antiarrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, beta-adrenoceptor blocking agents, blood products and substitutes, anti-cancer agents, cardiacinotropic agents, contrast media, corticosterioids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, vasidilators, neuron blocking agents, anticholinergic and cholinomimetic agents, antimuscarinic and muscarinic agents, vitamins, and xanthines.

The organic substance, such as biologically active material, e.g. a medicament, may be crystalline, amorphous or their mixtures.

Figure 1:
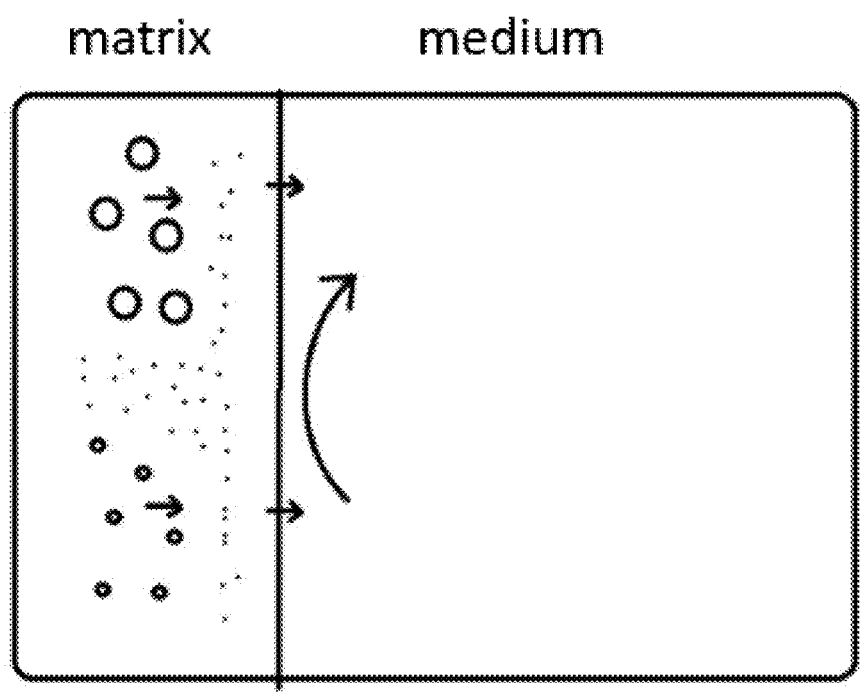
FIG. 1 shows the principle for discriminating the dissolved sample substance (dots) from undissolved sample substances (circles)

The invention is based on one or more lyophilic matrices that create conditions for discriminating the dissolved sample substance from undissolved sample substances. The principle is shown in FIG. 1, wherein the dissolved species (dots) diffuse significantly faster from the matrix towards the medium than the particles (circles).

The invention is aimed to prevent dispersion of the undissolved sample substance while it should present no significant membrane effect.

Accordingly, the invention is aimed to differentiate dissolution rates of small and large sample substance particles, such as nanoparticles and bulk material.

Small particles dissolve faster than large ones as stated in the Noyes-Whitney equation (1)

$$\frac{dm}{dt} = A\frac{D}{d}(C_s - C_b) \tag{1}$$

where m is the mass of dissolved material, t is time, A is surface area of the interface between the dissolving substance and the solvent, D is diffusion coefficient of the particle in the solvent, d is thickness of the boundary layer of the solvent at the surface of the dissolving substance, $C_s$ is mass concentration of the substance on the surface of the interface and $C_b$ is mass concentration of the substance in the bulk of the solvent.

The process of discrimination between undissolved particles and dissolved species is based on different diffusion velocities of particles compared to dissolved species (I. V. Fedsove et al., Measurement of the Diffusion Coefficient of Nanoparticles by Selective Plane Illumination Microscopy, Optics and Spectroscopy in Biomedical Investigations, Vol 107, No 6, 84-107, 2009). The diffusion velocity of nanoparticles according to the study of Fedsove et al. is less than 0.5 μm/s, whereas the diffusion of the dissolved species can be described with Fick's second law.

$$C(x, t) = \frac{1}{2}C_0\left\{\text{erf}\left[\frac{h-x}{2\sqrt{Dt}}\right] + \text{erf}\left[\frac{h-x}{2\sqrt{Dt}}\right]\right\} \tag{2}$$

where, x is location, t is time, C is concentration, D is diffusion coefficient, h is half of the diameter of the matrix, and erf is error function.

Figure 2A:
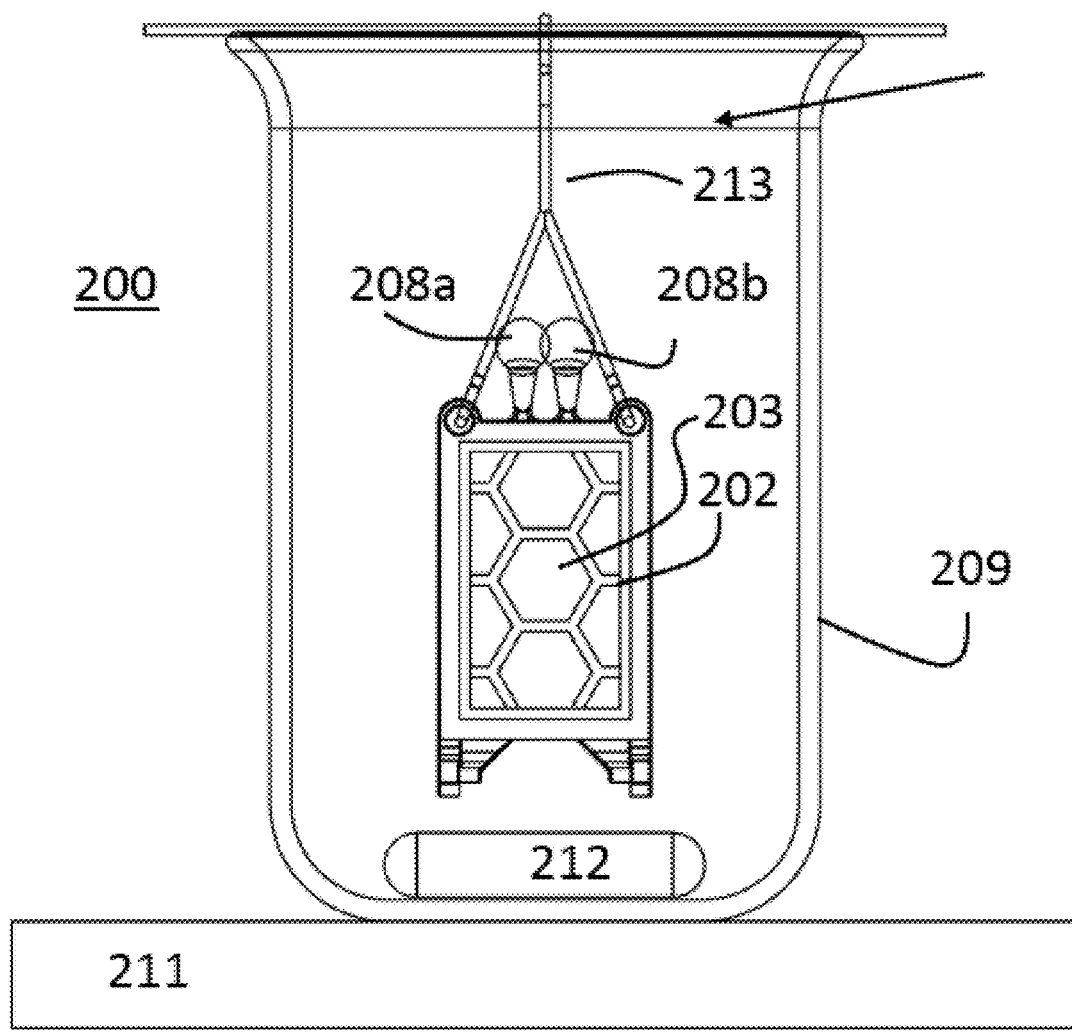
FIG. 2a illustrates a front view of a device according to exemplary non-limiting embodiment of the present invention.
Figure 2B:
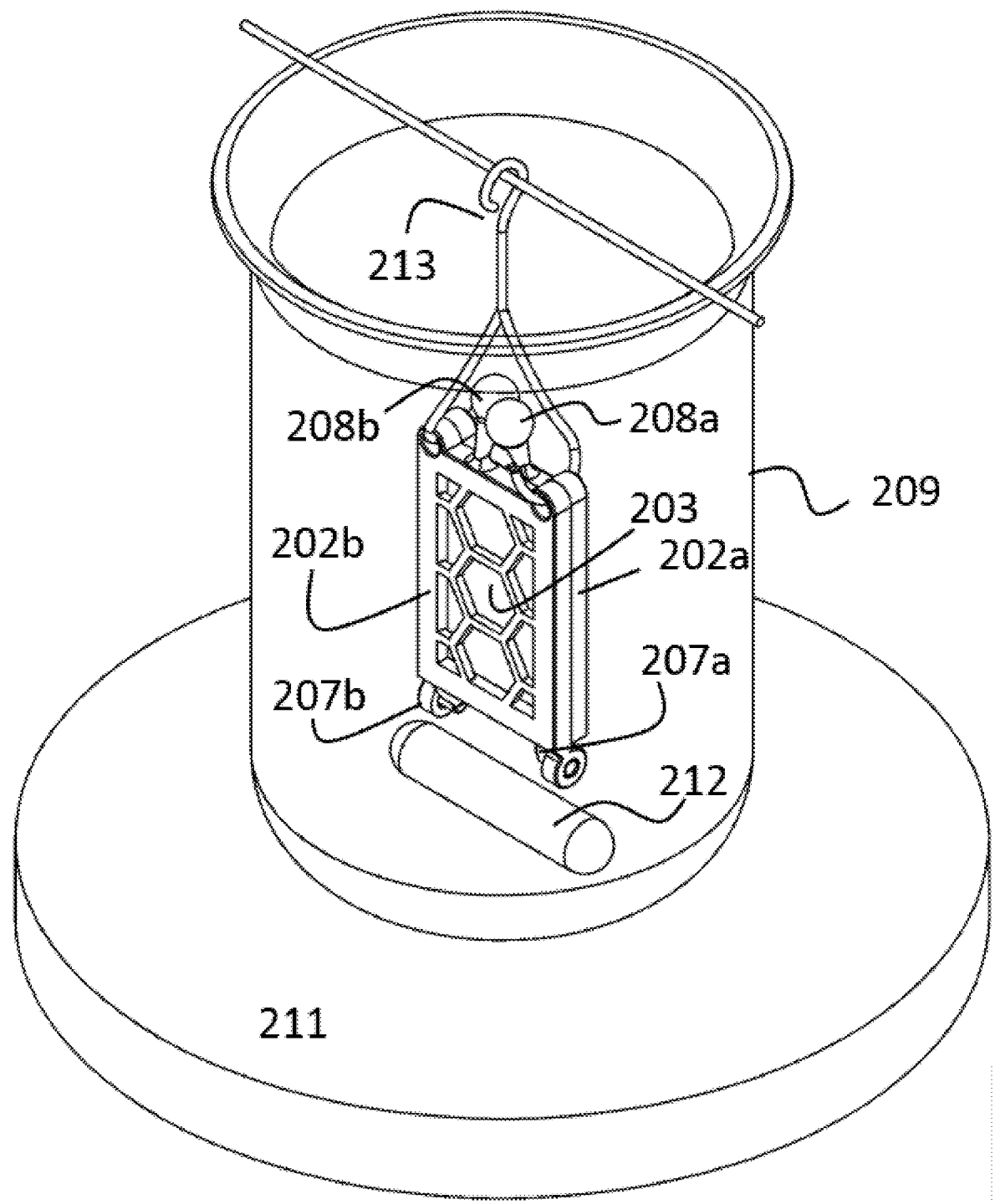
FIG. 2b illustrates a perspective view of a device according to exemplary non-limiting embodiment of the present invention.
Figure 2C:
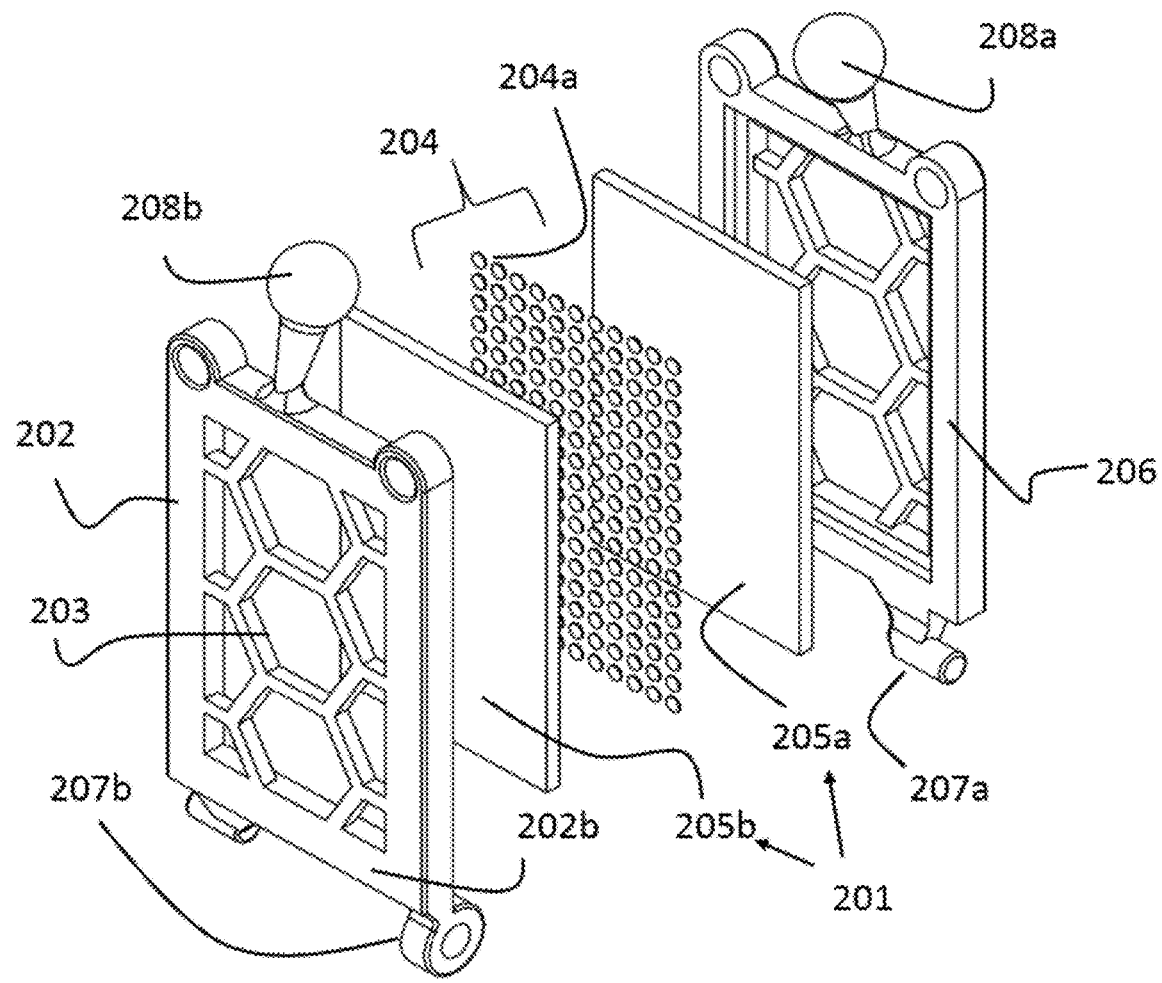
FIG. 2c illustrates exploded view of a device according to exemplary non-limiting embodiment of the present invention.

According to one embodiment the present invention concerns a device for dissolving a sample substance. An exemplary device is shown in FIGS. 2a-c. FIGS. 2a and 2b show front and perspective view of the device, respectively. FIG. 2c shows an exploded view of the device and a sample comprising a sample substance.

The exemplary device 200 includes a shell matrix 201 comprising a first lyophilic, preferably fibrous material, and a cage 202 comprising a plurality of holes. One of the holes is marked with a reference number 203. The hole(s) is/are preferably though the cage to allow sufficient medium flow through the cage. The shell matrix is adapted to cover the sample to form a shell matrix-sample system. FIG. 2c shows an exploded view of the device showing also a sample substance featuring a plurality of spots 204 one of which is shown as reference number 204a. The shell matrix-sample substance system is adapted to be inserted into the cage.

According to a preferable embodiment the shell matrix is in the form of two sheets 205a,b comprising the first lyophilic material that is preferably selected from cotton, cellulose and viscose, most preferably cotton. When the device is in operation, the sample substance is covered by the shell matrix, and a shell matrix-sample system is formed. The size of the shell matrix-sample system should be such that it fits into the cage, and preferably completely fills the cage.

The function of the cage is to maintain the geometry of the shell matrix-sample system even upon wetting. The geometry of the cage is chosen according to shell matrix-sample system, and is preferably spherical, cylindrical, spiral shaped, coil shaped, toroidal, conical, most preferably plate-like. The cage has preferably a frame 206 to apply pressure on the sides of the core-shell system to prevent leaking from the sides. The compression level introduced by the frame on the matrix is preferably moderate, more preferably adequate to maintain the geometry as the shell matrix-sample system is exposed to dissolution media.

The cage comprises preferably plurality of holes, a.k.a 'eyes'. The eye size of the cage is preferably such that the eye area is 90% of the cage area on the matrix surface. The number of eyes of the cage is at least one, preferably less than 10 but higher than 3 to produce sufficiently divided compression to the matrix and to prevent changes in the cage geometry. Exemplary combinations for controlling the matrix geometry are: size and density of cotton used, dimensions of the cage and eye size and number. The cage is preferably manufactured of inert material, more preferably inert metal, most preferably material that is not affected by ultrasound or electric field. Exemplary suitable cage materials are stainless steel, plastic, or glass.

According to a preferable embodiment the cage comprises means to position the shell matrix-sample system in the cage. The cage comprises preferably means, such as locking elements, adapted press and/or keep the shell matrix-sample system inside the cage in a substantially constant volume and shape. According to an exemplary embodiment shown in FIG. 2a-c, the cage comprises a first part 202a comprising a first hinge element 207a and a first locking element 208a, and a second part 202b comprising a second hinge element 207b and a second locking element 208b, the first part adapted to fit to the second part. According to the embodiment the hinges and the locking elements also act as means to keep the shell matrix-sample system at substantially constant volume and shape, and/or to avoid the shell matrix-sample system from expanding upon wetting.

It is essential that the shell matrix comprises lyophilic fibrous material. A suitable matrix should wet thoroughly when exposed to the dissolution medium. As the sample substance is within the matrix, it should be surrounded practically immediately by the dissolution medium. Optimally, the only lag time present in the dissolution process is caused by the delay of the diffusion of the dissolved species.

The immediate wetting provides conditions where the dissolution medium can freely access the matrix. An important property of the matrix is perfusion. Accordingly, the lyophilic material suitable for the present invention should be able to uptake at least five times more solvent than its own weight. Exemplary first lyophilic fibrous materials are cotton, cellulose, and viscose. A preferable material is cotton that can take up water 10-12 times its weight.

According to one embodiment the device further comprises a vessel 209 for holding a medium capable of dissolving the sample substance. The vessel is preferably equipped with agitating means 210, such as a magnetic stirrer 211 and a stir bar 212. The size of the vessel is preferably such that the whole cage fits into the vessel and the cage is immersed into the dissolution medium. The device shown in FIGS. 2a,b further comprises means 213 adapted to hold the device at a constant position in the vessel.

Figure 3:
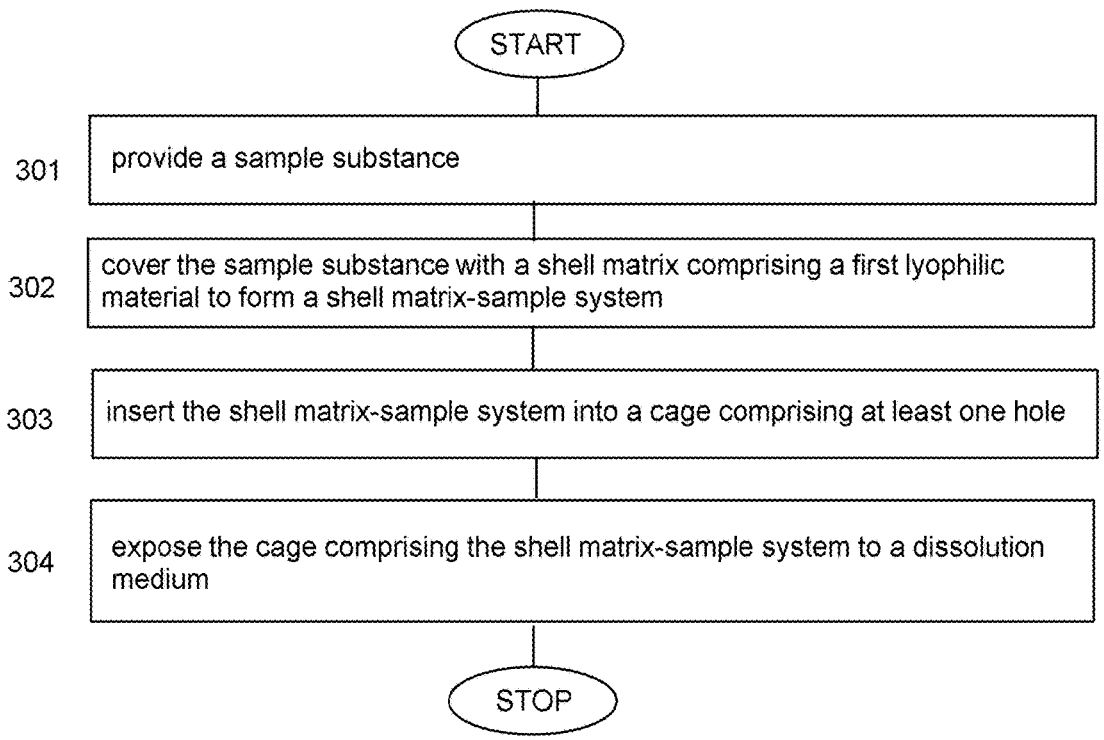
FIG. 3 illustrates a flow chart of the method of the present invention for dissolving a sample substance.

According to another embodiment the present invention concerns a method for dissolving a sample substance. A flow chart of the method for dissolving a sample substance according to the present invention is shown in FIG. 3. An exemplary device suitable for the method is shown in FIG. 2a-c. The method comprises the following actions:
- action 301: providing a sample substance,
- action 302: covering the sample substance with a shell matrix comprising a first lyophilic material to form a shell matrix-sample system
- action 303: positioning the shell matrix-sample system into a cage comprising at least one hole, and
- action 304: exposing the cage comprising the shell matrix-sample system to a medium capable of dissolving the sample substance.

Accordingly, the sample substance is first covered with a shell matrix comprising a first lyophilic, preferably fibrous material to form a shell matrix-sample system. Exemplary first lyophilic fibrous materials are cotton, cellulose, and viscose. A preferable material is cotton.

According to a particular embodiment, the shell matrix comprises two, preferably identical, sheets of lyophilic material, such as cotton, and the sheets are pressed against the sample.

Next, the shell matrix-sample system is inserted into a cage comprising at least one, preferably plurality of holes. The geometry of the cage is chosen according to the shell matrix-sample system, and its function is to maintain the geometry of shell matrix-sample system even upon wetting. The cage geometry is preferably spherical, cylindrical, spiral shaped, coil shaped, toroidal, conical, most preferably plate-like. The cage has preferably a frame to apply pressure on the sides of the shell matrix-sample system to prevent leaking from the sides. The force introduced by the frame on the matrix is preferably moderate, more preferably adequate to maintain the geometry as the matrix is inserted into dissolution media.

According to the method, the cage comprising the shell matrix-sample system is exposed e.g. by immersing into a vessel comprising a dissolution medium capable of dissolving the sample substance. An exemplary dissolving medium for hydrophilic matrices is phosphate buffered saline. Further exemplary dissolving media for lyophilic matrices comprising one or more sample substances are organic solvents, such as octane, hexane, dichloromethane, chloroform, pyridine, THF, diethyl ether, toluene, benzene, methanol, ethanol, propanol, and mixtures thereof.

When the cage is exposed to a dissolution medium, the dissolution medium flows through the one or more holes towards the sample substance and dissolves it. The arrow in FIG. 2a shows surface level of the dissolution medium.

According to a preferable embodiment, the sample substance, prior to covering with the shell matrix, is admixed with a second lyophilic, preferably fibrous material. The admixing may be performed by grinding or shaking, more preferably by mixing, in such a manner that the sample substance e.g. sample substance particles are attached to the matrix material. Adhesion to matrix is achieved preferably by hydrogen bonding. Exemplary second lyophilic materials are cotton, cellulose, and viscose. A preferable second lyophilic material is cotton.

It is essential that the first and the second matrix comprises lyophilic fibrous material. A suitable matrix should wet thoroughly when exposed to the dissolution medium. As the sample substance is inside the matrix, it is surrounded immediately with dissolution medium. Optimally, the only lag time present in the dissolution process is caused by the delay of the diffusion of the dissolved species. The dissolution can be enhanced by agitating the dissolution medium, e.g. by stirring, mixing, shaking or sonicating.

The immediate wetting provides conditions where the dissolution medium can freely access the matrices. An important matrix property is perfusion. Accordingly, the lyophilic material suitable for the present invention should be able to take up solvent at least five times its own weight. Exemplary first and the second lyophilic fibrous materials are cotton, cellulose, and viscose. A preferable material is cotton that is able to take up water 10-12 times its own weight.

Figure 4:
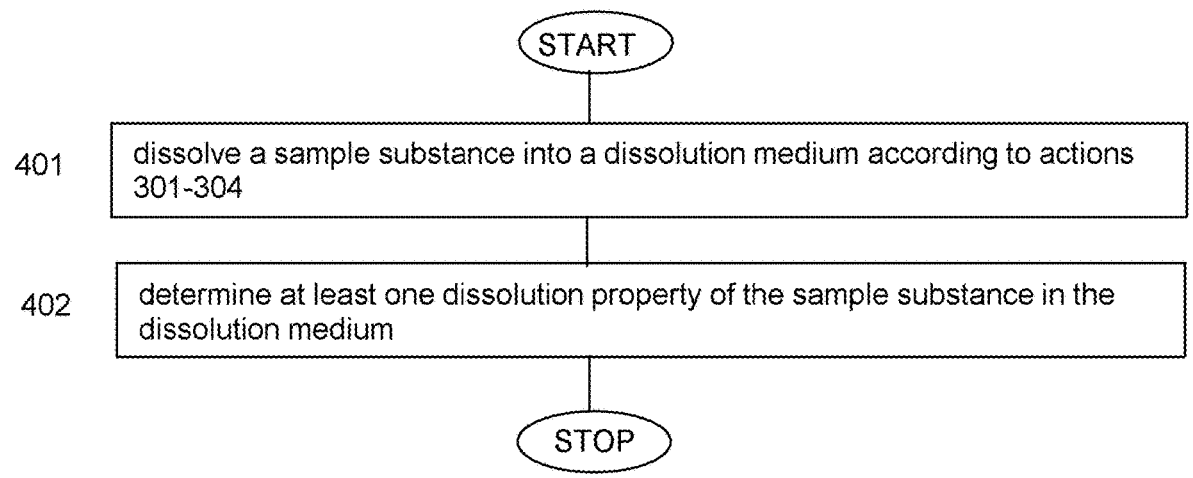
FIG. 4 illustrates a flow chart of a method of the present invention for determining one or more dissolution properties of a sample substance.

According to another embodiment the present invention relates to a method for determining one of more dissolution properties of a sample substance. A flow chart of the method is shown in FIG. 4. The method comprises the following actions
- action 401: dissolving the sample substance into a dissolution medium by a method according to any of claims 6-13, and
- action 402: determining at least one dissolution property of the sample substance in the dissolution medium.

Detection of the dissolved species is done preferably by UV-vis, mass, NIR, IR, Raman or spectroscopy, imaging, change in refractive index, and detection of radioactive compounds. The detection can be done in offline or online analysis, preferably as a function of time.

When the determining the quantity of the dissolved special is done offline, it is performed preferably without disturbing the hydrodynamics of the dissolution vessel, i.e. near the surface of the dissolution medium.

If the matrices do not disturb the detection method, the dissolved and/or the undissolved species of the sample substance can be detected also within the matrix. Additionally, light scattering methods may be combined to determine and to ensure that the medium is free from undissolved particles or recrystallized species within the medium.

Figure 5:
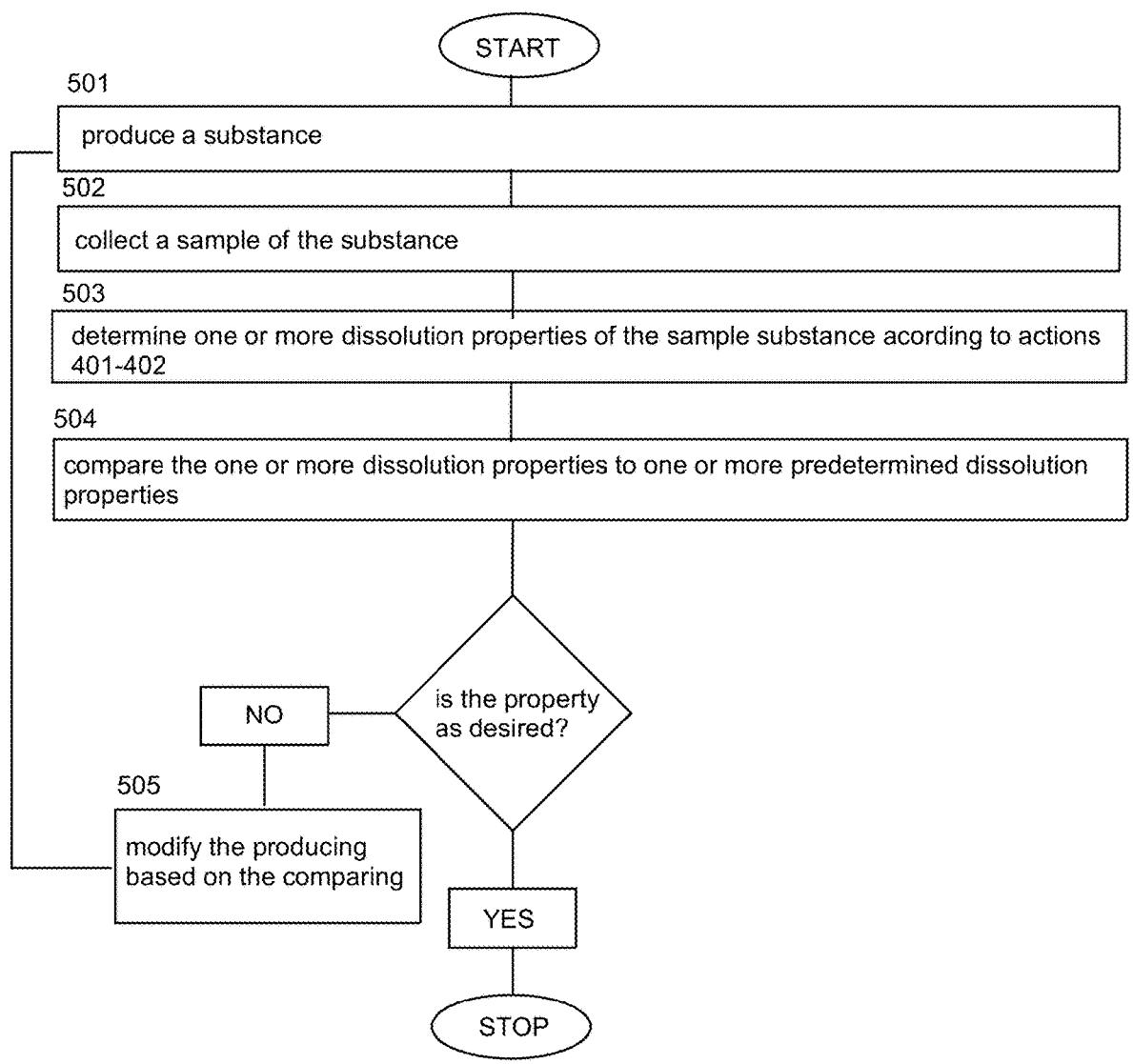
FIG. 5 illustrates a flow chart of a method of the present invention for nanonization optimization and/or quality control.

According to another embodiment, the present invention concerns a method for controlling a process for producing a substance. A flow chart of the method is shown in FIG. 5. The method comprises the following actions:
- action 501: producing a substance,
- action 502: providing a sample substance by collecting a sample of the substance,
- action 503: determining one or more dissolution properties of the sample substance according to claim 13,
- action 504: comparing the one of more dissolution properties of the sample substance to one or more predetermined dissolution properties the substance, and
- action 505: optionally modifying the producing based on the comparing.

An exemplary device and method suitable for producing the substance according to action 501 is disclosed in WO2016055696, incorporated herein in reference. The document discloses a method for preparing nanoparticles by using a gradient pressure reduction process that creates conditions for controlled expansion of supercritical solutions. The method disclosed therein comprises admixing a substance and a supercritical fluid to form a mixture at a first pressure, decreasing the first pressure gradually to a second pressure in such a manner that a flow of the mixture is formed and nucleation of the substance in the mixture is initiated, and decreasing the second pressure to a third pressure in such a manner that solidification of the fluid of the mixture, comprising the nucleated sample substance, is initiated.

According to an exemplary embodiment the sample of the substance, preferably nucleated substance produced as disclosed in WO2016055696, is collected and preferably admixed with the second lyophilic material of the present invention, prior to determining one of more of its dissolution properties.

According to a particular embodiment, one or more dissolution properties of the sample substance is determined, and compared to one or more predetermined dissolution properties of the sample substance. For determining, at least one dissolution property of the sample substance, such as concentration in dissolution medium, is analyzed by using any suitable method known in the art. Exemplary methods are HPLC and UV-vis.

The process for producing the substance can be modified, if needed based on the comparing. The modifying comprises typically changing one or more of process parameters. For modifying, one or more of process parameters are changed until the determined dissolution property is as desired. For example, if the dissolution rate of the sample substance is slower than desired, one of more of the process parameters are changed until the desired dissolution rate is achieved. Exemplary process parameters disclosed in WO2016055696 include, but are not limited to, the nature of a supercritical fluid, one or more pressures, and temperature.

According to still another embodiment, the present invention concerns a kit for use in a method according the present invention. The kit comprises a device according to any of claims 1-5, and a lyophilic material for the sample substance. Exemplary lyophilic materials are cotton, cellulose, and viscose. A preferable material is cotton.

Experimental

The model compound in the dissolution experiments with the exemplary device was indomethacin (Hawkins, Minn., USA). Indomethacin was milled with a Fritsch Pulverisette 7 Premium ball mill (Fritsch GmbH, Idar-Oberstein, Germany) to produce nanoparticles. The nanoparticles were prepared also by using the device and method disclosed in WO2016055696.

60 g of milling pearls (zirconium oxide, diameter 1 mm) and 2.00±0.05 g indomethacin suspended in 5.0 ml 0.24 g/ml poloxamer 188 (BASF Co., Ludwigshafen, Germany) solution (60 wt % relative to the drug amount) was added to the milling bowl. Additional 5 ml of water was used to collect the residual suspensions from the beaker to the milling bowl. The suspension was grinded at 850 rpm in 5 grinding cycles of 3 min.

The cotton used was 100% cotton prepared without bleach. The matrix material should not contain traces of any chemicals. Stainless steel cages were designed with SolidWorks and 3D printed with selective laser sintering. 100 mL containers with 10.5 cm diameter were used as vessels.

Three parallel tests were conducted for both bulk indomethacin and the indomethacin nanoparticles. The mass of particles and core matrix was normalized for each experiment and materials. The drug compound was evenly distributed within the core cotton (second lyophilic material), and was placed between the shell parts of the matrix (first lyophilic material).

Distribution of nanoparticles was done by wetting the second lyophilic material with nanosuspension of known indomethacin concentration, consisting of water, co-polymer, and indomethacin. The suspension was mixed evenly within the second lyophilic material and the second lyophilic material was left to dry.

Bulk sample was prepared by mixing quantities, corresponding to those of the suspension, of the bulk indomethacin and co-polymer with the second lyophilic material in a mortal without grinding to evenly distribute the bulk indomethacin and the co-polymer in the second lyophilic material.

Dissolution tests were conducted in glass vessels under heating and stirring (IKA RT 15 P, IKA Werke GmbH & CO. KG, Staufen, Germany) in pH 5.5 phosphate buffer media prepared according to the instructions of the European Pharmacopeia (European Pharmacopoeia Online 8.8). The temperature was monitored during the dissolution tests and kept at 37.0±0.5° C. under magnetic stirring of 180 rpm. The volume of the phosphate buffer media was 100 mL. Each aliquot was 1 mL and it was replaced with the same volume of fresh media. Aliquots were taken at the time points 30 s, 1 min, 2 min, 5 min, 10 min, 30 min, 1 h, 2 h, 3 h, 4 h, 6 h and 24 h.

Samples were analyzed with high performance liquid chromatography (HPLC Thermo System Products, Agilent 1200 Infinity Series, Agilent Technologies, Germany). Discovery C18, 4.6×150 mm, 5 μm (Supelco, Bellefonte, USA), flow rate of 1.5 mL/min with a mobile phase consisting of 60:40 (v/v) acetonitrile (ACN) and 0.2% ortophosphoric acid ($H_3PO_4$) in water (milliQ) were used operating at 30° C. A standard curve for indomethacin quantification was made in triplicate from indomethacin concentrations of 0.08-500 mg/L ($R^2$=0.999).

Figure 6:
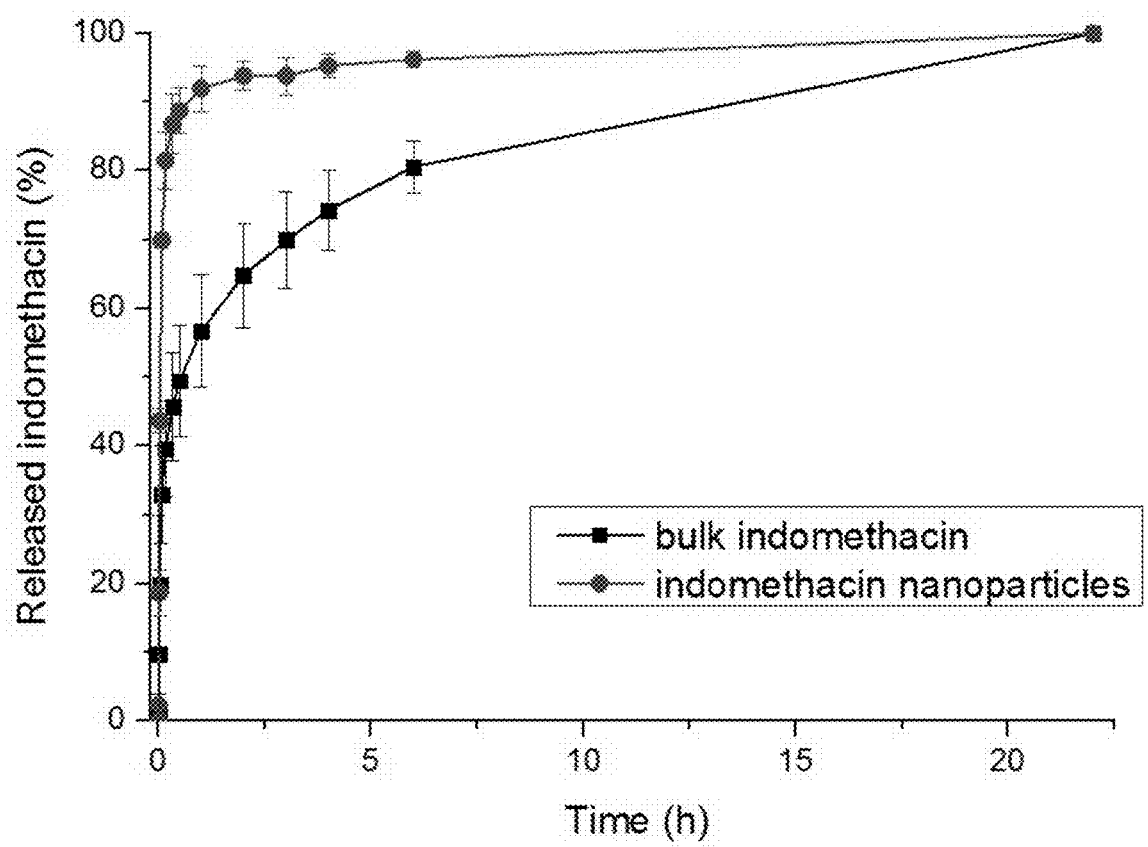
FIG. 6 shows cumulative percentage of indomethacin released in 22 hours in pH 5.5 phosphate buffer.
Figure 7:
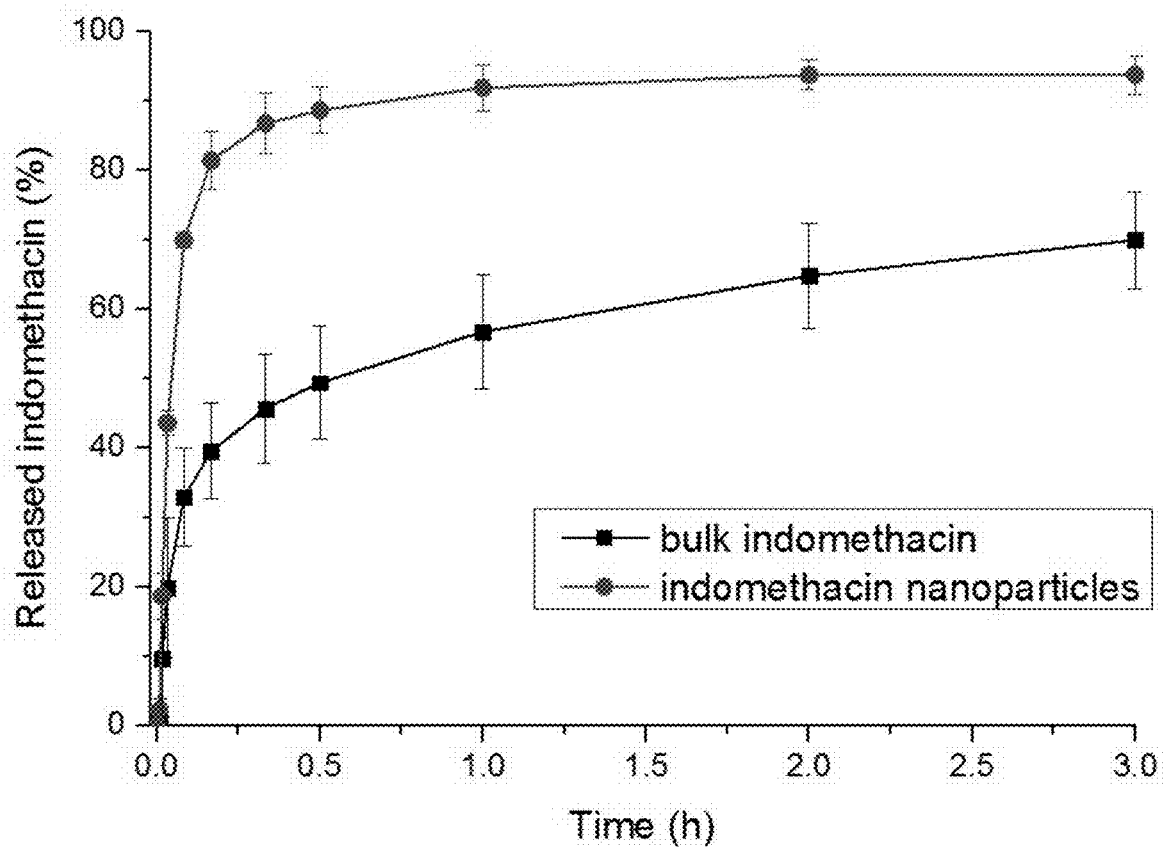
FIG. 7 shows cumulative percentage of indomethacin released in 3 hours in pH 5.5 phosphate buffer.
Figure 8:
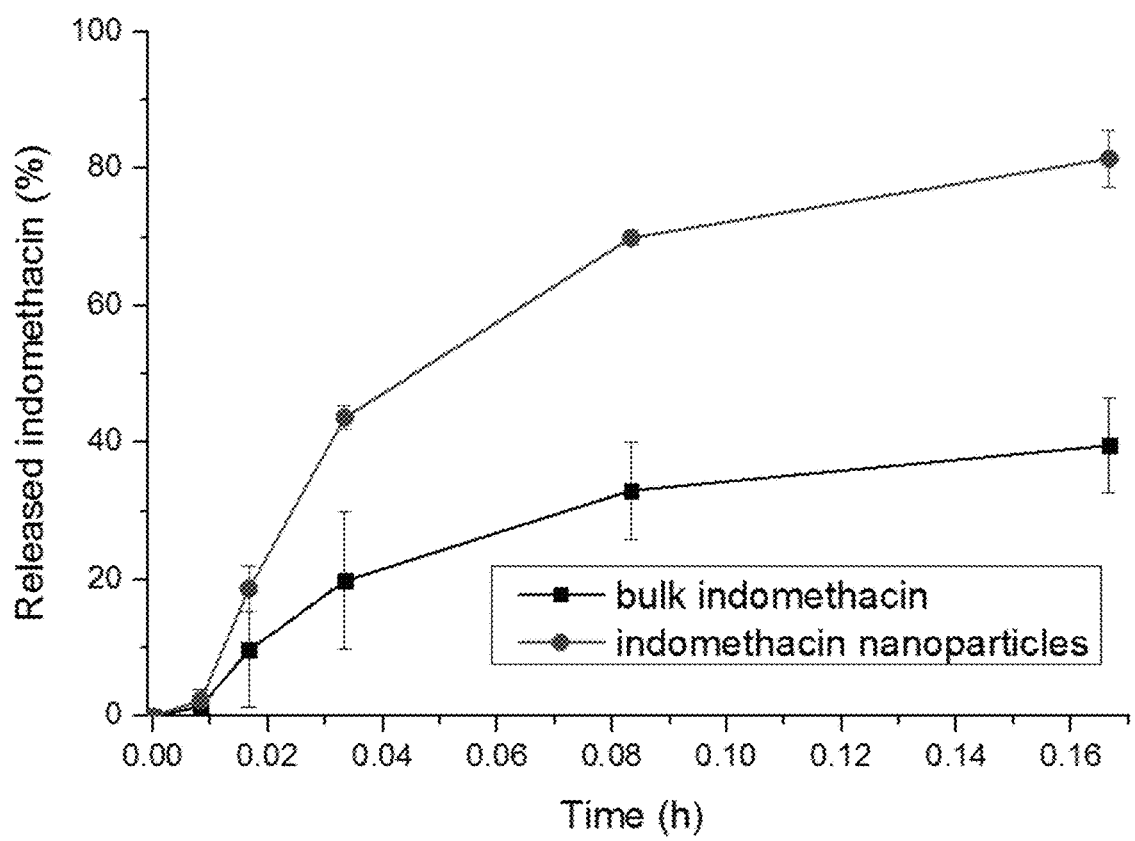
FIG. 8 shows cumulative percentage of indomethacin released in 20 minutes in pH 5.5 phosphate buffer.

The cumulative fraction of released indomethacin is presented up to 22 h in FIG. 6, up to 3 h in FIG. 7, and up to 30 min FIG. 8. As seen, from the figures, milled nanoparticles exhibit a narrower size-distribution than the bulk material. Thus, the standard deviation that can be seen as error bars, in FIGS. 6-8, indicates that the effect of particle size-distribution on the bulk material is more significant than that of the nanoparticles. This further indicates that the method is more sensitive to particle size distribution than the conventional methods.

The specific examples provided in the description given above should not be construed as limiting the scope and/or the applicability of the appended claims.

What is claimed is:

1. A method for dissolving sample substance particles, the method comprising, in the following order:
   providing sample substance particles, then
   admixing the sample substance particles with a second lyophilic material, thereby attaching the sample substance particles to the second lyophilic material, to form a core matrix, then
   covering the core matrix with a shell matrix in the form of two sheets comprising a first lyophilic material, wherein the covering comprises pressing the two sheets against t he core matrix with one sheet pressed against one side of the core matrix and the other sheet pressed against an opposite side of the core matrix to form a shell matrix-core matrix system, wherein the first lyophilic material and the second lyophilic material are each selected from cotton, cellulose, and viscose, preferably cotton, then
   inserting the shell-core matrix system into a cage comprising at least one hole, then
   exposing the cage comprising the shell matrix-core matrix system to a dissolution medium capable of dissolving the sample substance particles, then
   allowing the dissolution medium to flow through the at least one hole towards the sample substance particles, and then dissolving said particles in the dissolution medium.

2. The method according to claim 1, wherein the inserting comprises pressing the shell matrix-core matrix system to take the shape of the cage.

3. The method according to claim 1, wherein the exposing comprises immersing the cage into the dissolution medium capable of dissolving the sample substance particles.

4. The method according claim 1 comprising agitating the dissolution medium capable of dissolving the sample substance particles.

5. A method for determining one or more dissolution properties of sample substance particles, the method comprising
   dissolving the sample substance particles into a dissolution medium capable of dissolving the sample substance particles by the method according to claim 1, and
   determining at least one dissolution property, such as concentration, of the sample substance particles in the dissolution medium, preferably as a function of time.

6. A method for controlling a process for producing substance particles, the method comprising,
   (i) producing the substance particles,
   (ii) providing sample substance particles by collecting a sample of the substance particles,
   (iii) determining one or more dissolution properties of the sample substance particles according to claim 5,
   (iv) comparing the one or more dissolution properties of the sample substance particles to one or more predetermined dissolution properties.

7. The method according to claim 6 further comprising
   (v) modifying the producing by changing one or more process parameters of said process based on the comparing.

* * * * *